(12) United States Patent
Yonai et al.

(10) Patent No.: US 12,013,177 B2
(45) Date of Patent: Jun. 18, 2024

(54) CONTAINER FOR CRYOPRESERVATION AND TRANSPORTATION

(71) Applicant: TAIYO NIPPON SANSO CORPORATION, Tokyo (JP)

(72) Inventors: Hajime Yonai, Tokyo (JP); Akira Mase, Tokyo (JP); Hirotsugu Takeuchi, Tokyo (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 121 days.

(21) Appl. No.: 17/800,076

(22) PCT Filed: Mar. 2, 2021

(86) PCT No.: PCT/JP2021/007818
§ 371 (c)(1),
(2) Date: Aug. 16, 2022

(87) PCT Pub. No.: WO2021/177265
PCT Pub. Date: Sep. 10, 2021

(65) Prior Publication Data
US 2023/0097551 A1 Mar. 30, 2023

(30) Foreign Application Priority Data

Mar. 6, 2020 (JP) ................................ 2020-039093
Mar. 6, 2020 (JP) ................................ 2020-039094

(51) Int. Cl.
*F25D 3/10* (2006.01)
*B65D 81/38* (2006.01)

(52) U.S. Cl.
CPC ......... *F25D 3/105* (2013.01); *B65D 81/3806* (2013.01); *B65D 81/3809* (2013.01); *F25D 2201/14* (2013.01)

(58) Field of Classification Search
CPC . F25D 3/105; F25D 2201/14; B65D 81/3806; B65D 81/3809; A47J 41/0044; C12M 45/22
See application file for complete search history.

(56) References Cited

U.S. PATENT DOCUMENTS

| 7,581,407 B1 | 9/2009 | Romanos et al. |
| 2002/0083717 A1 | 7/2002 | Mullens et al. |
| 2019/0150427 A1 | 5/2019 | McCormick |

FOREIGN PATENT DOCUMENTS

| CA | 2916196 | 12/2014 | |
| FR | 2933476 A1 * | 1/2010 | ............ F17C 3/085 |

(Continued)

OTHER PUBLICATIONS

International Search Report for PCT/JP2021/007818, mailed May 18, 2021, 6 pages.

(Continued)

*Primary Examiner* — Emmanuel E Duke
(74) *Attorney, Agent, or Firm* — Nixon & Vanderhye P.C.

(57) ABSTRACT

An object of the present invention is to provide a container for cryopreservation and transportation which is excellent in maintainability and can appropriately control the temperature of an object to be frozen. The present invention provides a container for cryopreservation and transportation used to transport an object to be frozen, including: a thermal insulation container having an upper opening; a thermal insulation lid which closes the upper opening of the thermal insulation container; and a cooling unit which is held in the thermal insulation container while absorbing liquid nitrogen, wherein a housing space for accommodating a storage tool for storing the object to be frozen is provided inside the thermal insulation container, and the cooling unit is detachable through the upper opening of the thermal insulation (Continued)

container while the storage tool located in the housing space is housed in the thermal insulation container.

11 Claims, 17 Drawing Sheets

(56) References Cited

FOREIGN PATENT DOCUMENTS

| | | | | |
|---|---|---|---|---|
| JP | 53-152259 | 11/1978 | | |
| JP | 2008-105720 | 5/2008 | | |
| JP | 2011-240939 | 12/2011 | | |
| JP | 4881046 | 2/2012 | | |
| JP | 2013-103747 | 5/2013 | | |
| JP | 2013103747 A | * | 5/2013 | |
| JP | 2015-010868 | 1/2015 | | |
| JP | 2016-186399 | 10/2016 | | |
| JP | 2016186399 A | * | 10/2016 | |
| JP | 2017-100857 | 6/2017 | | |
| JP | 2017-165487 | 9/2017 | | |
| WO | WO-02053967 A1 | * | 7/2002 | ............ F17C 13/006 |
| WO | WO-2017083164 A1 | * | 5/2017 | |
| WO | WO-2019099803 A1 | * | 5/2019 | ........... A01N 1/0257 |

OTHER PUBLICATIONS

Written Opinion of the ISA for PCT/JP2021/007818, mailed May 18, 2021, 4 pages.
Extended European Search Report mailed Apr. 16, 2024 in European Application No. 21764405.3, 8 pages.

* cited by examiner

CONTAINER FOR CRYOPRESERVATION AND TRANSPORTATION

This application is the U.S. national phase of International Application No. PCT/JP2021/007818 filed Mar. 2, 2021, which designated the U.S. and claims priority to JP 2020-039093 filed Mar. 6, 2020, JP 2020-039094 filed Mar. 6, 2020, the entire contents of each of which are hereby incorporated by reference.

TECHNICAL FIELD

The present invention relates to a container for cryopreservation and transportation of an object to be frozen.

BACKGROUND ART

For example, in medical fields such as infertility treatment and regenerative medicine, and in research fields such as the development of new drugs, in order to prevent deterioration of biological samples such as sperm, egg cells, embryos, blood, and cells (hereinafter, simply referred to as "sample"), the sample is generally cryopreserved. For cryopreservation, a cryopreservation container containing liquid nitrogen (boiling point: −196° C.) is widely used because the sample can be stored in a stable state for a long period of time. Further, it is also required to freeze and store articles for example, medicines such as cell-based drugs, small molecule drugs, and vaccines, drugs such as chemical substances, and foods in an ultra-low temperature environment. Hereinafter, an object to be frozen such as a sample or an article is referred to as "object to be frozen".

Further, as the cryopreservation container, there is a dry shipper (container for cryopreservation and transportation) used for transporting an object to be frozen (see, for example, Patent Document 1 below). The dry shipper includes a thermal insulation container having an upper opening, a thermal insulation lid that closes the upper opening of the thermal insulation container, and an absorbent material that absorbs liquid nitrogen.

In the dry shipper, liquid nitrogen is held in the thermal insulation container in a state of being absorbed by the absorbent material, so even if the thermal insulation container collapses, there is no concern that liquid nitrogen will leak to the outside through the upper opening of the thermal insulation container. Therefore, it is possible to transport an object to be frozen more safely while keeping the temperature inside the thermal insulation container at an ultra-low temperature (−150° C. or lower).

PRIOR ART DOCUMENTS

Patent Documents

Patent Document 1: Japanese Patent No. 4881046

SUMMARY OF INVENTION

Problem to be Solved by the Invention

The conventional dry shipper explained above is used in a state at which liquid nitrogen is absorbed by an absorbent material attached to the inside of the thermal insulation container. Therefore, since the absorbent material cannot be removed, it is difficult to perform maintenance such as cleaning and disinfection of the inside of the thermal insulation container after use. In addition, although the dry shipper is used repeatedly, in order to improve the absorption efficiency of liquid nitrogen, it is necessary to dry the absorbent material sufficiently after use and then absorb the liquid nitrogen into the absorbent material before use.

In addition, in the dry shipper, the liquid nitrogen absorbed by the absorbent material becomes a gas phase state in the thermal insulation container and gradually decreases. Therefore, if the liquid nitrogen absorbed by the absorbent material decreases, it is necessary for the absorbent material to reabsorb liquid nitrogen. In this case, it is necessary to temporarily remove the storage tool such as the canister that stores an object to be frozen from the thermal insulation container. Furthermore, in order to control the temperature of an object to be frozen, it is necessary to promptly transfer the storage equipment taken out from the thermal insulation container to another cryopreservation container or the like.

The present invention has been proposed in view of such conventional circumstances, and an object of the present invention is to provide a container for cryopreservation and transportation which is excellent in maintainability and can appropriately control the temperature of an object to be frozen.

Means for Solving the Problem

In order to achieve the object, the present invention provides the following container for cryopreservation and transportation.

[1] A container for cryopreservation and transportation of an object to be frozen including:
    a thermal insulation container having an upper opening;
    a thermal insulation lid which closes the upper opening of the thermal insulation container; and
    a cooling unit which is held in the thermal insulation container while absorbing liquid nitrogen,
    wherein a housing space for accommodating a storage tool for storing the object to be frozen is provided inside the thermal insulation container, and
    the cooling unit is detachable through the upper opening of the thermal insulation container while the storage tool located in the housing space is housed in the thermal insulation container.

[2] The container for cryopreservation and transportation according to [1],
    wherein the cooling unit is provided with a through hole for partitioning the housing space in the vertical direction.

[3] The container for cryopreservation and transportation according to [1],
    wherein the cooling unit includes a cooling portion which is provided with an absorbent material that absorbs liquid nitrogen, and a thermal insulation portion which is located on the cooling portion and provided with a thermal insulation material.

[4] The container for cryopreservation and transportation according to [3],
    wherein the cooling unit includes a fixing portion which is located on the thermal insulation portion and fixed to the upper portion of the thermal insulation container.

[5] The container for cryopreservation and transportation according to [1],
    wherein a plurality of the cooling units are provided so as to surround the housing space.

[6] The container for cryopreservation and transportation according to [1], wherein a support portion for supporting the storage tool is provided at the inner bottom portion of the thermal insulation container.

[7] The container for cryopreservation and transportation according to [6],
wherein the support portion is in contact with the cooling unit which is held in the thermal insulation container to restrict the movement of the cooling unit in the radial direction of the thermal insulation container.

[8] The container for cryopreservation and transportation according to [1],
wherein the cooling unit includes a cooling portion which is provided with an absorbent material that absorbs liquid nitrogen, a thermal insulation portion which is provided with a thermal insulation material and located on the cooling portion, and a positioning portion which is located on the thermal insulation portion,
a guide member is provided at the upper portion of the thermal insulation container.
the guide member includes a guide portion having a shape corresponding to the positioning portion, and
the cooling unit is guided in the vertical direction of the thermal insulation container along the guide member, the positioning portion is located inside the guide portion, and the cooling unit is positioned with respect to the guide member.

[9] The container for cryopreservation and transportation according to [8],
wherein a pressing member is detachably provided at the upper portion of the guide member, and
the pressing member is into contact with the cold insulation unit which is held in the thermal insulation container to restrict the movement of the cold insulation unit in the vertical direction of the thermal insulation container.

[10] The container for cryopreservation and transportation according to [1],
wherein the thermal insulation lid is provided with a thermal insulation convex portion to be inserted into the housing space.

[11] The container for cryopreservation and transportation according to [1],
wherein the thermal insulation container has a vacuum insulated structure.

Effects of the Invention

According to the present invention, it is possible to provide a container for cryopreservation and transportation which is excellent in maintainability and can appropriately control the temperature of an object to be frozen.

BRIEF DESCRIPTION OF DRAWINGS

FIG. 6 is a half cross-sectional view showing a state at which a plurality of cooling units are held in a thermal insulation container.

DETAILED DESCRIPTION OF THE PREFERRED EMBODIMENTS

Hereinafter, embodiments of the present invention will be described in detail with reference to the figures.
Note that the materials and the like exemplified in the following description are examples, and the present invention is not necessarily limited thereto, and the present invention can be appropriately modified and carried out without changing the gist thereof.

First Embodiment

Figure 1:
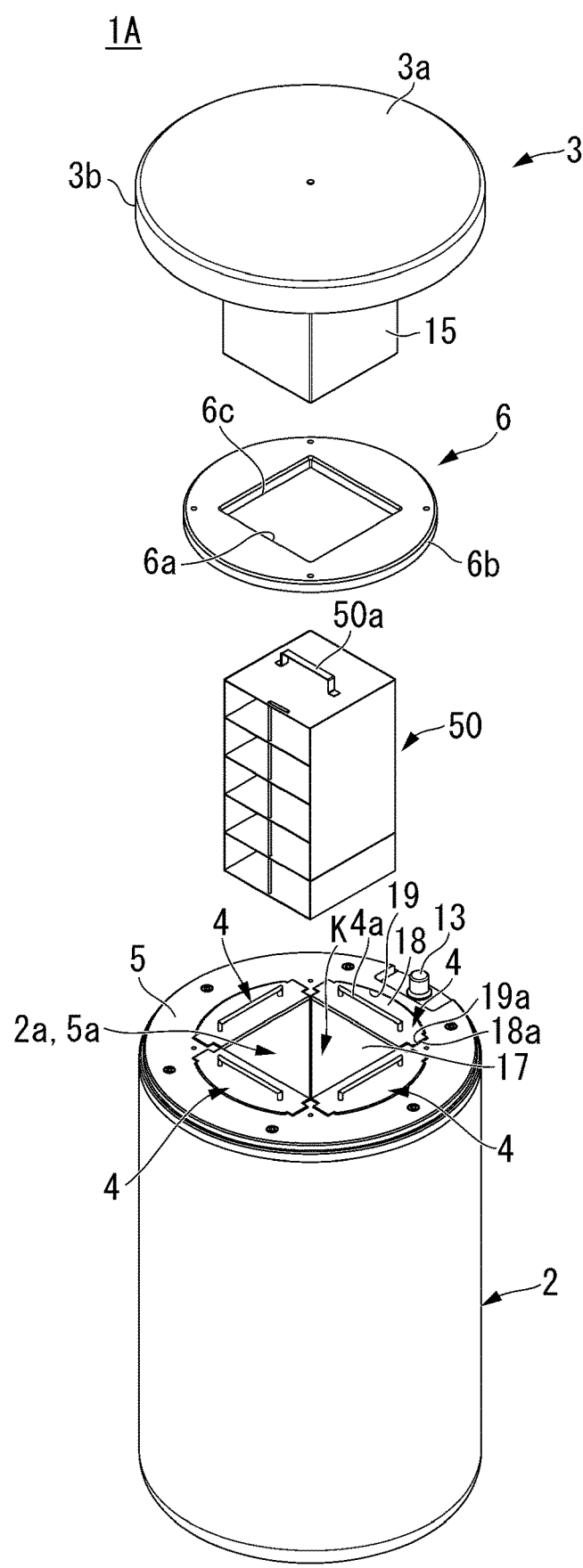
FIG. 1 is an exploded perspective view showing a dry shipper and a storage tool according to a first embodiment of the present invention.
Figure 2:
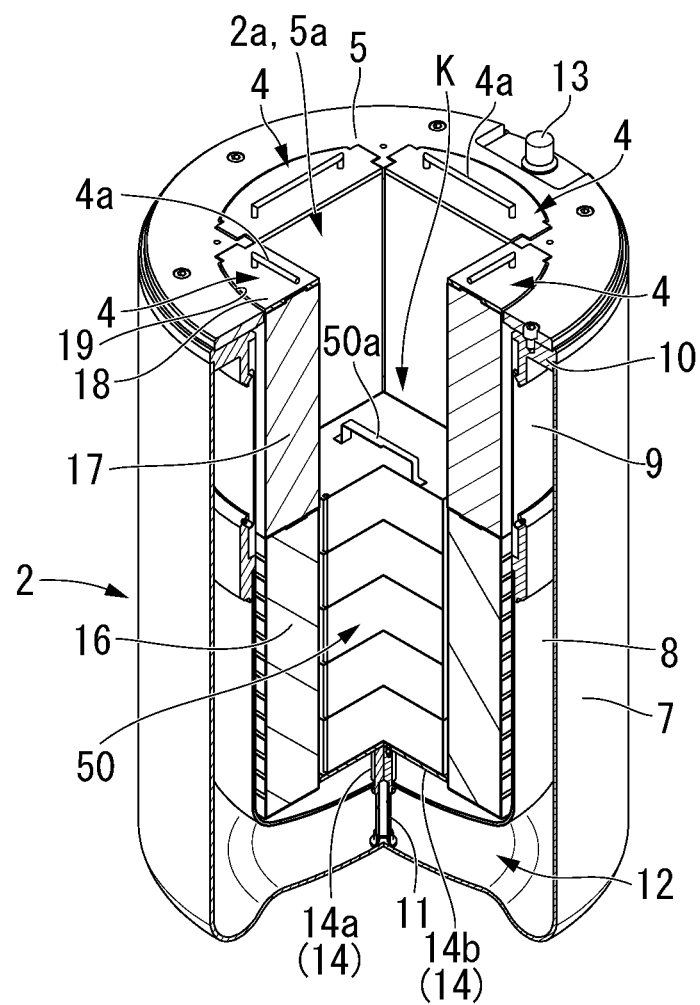
FIG. 2 is a partial cross-sectional perspective view showing a state at which the storage tool in the dry shipper shown in FIG. 1 is housed.
Figure 3:
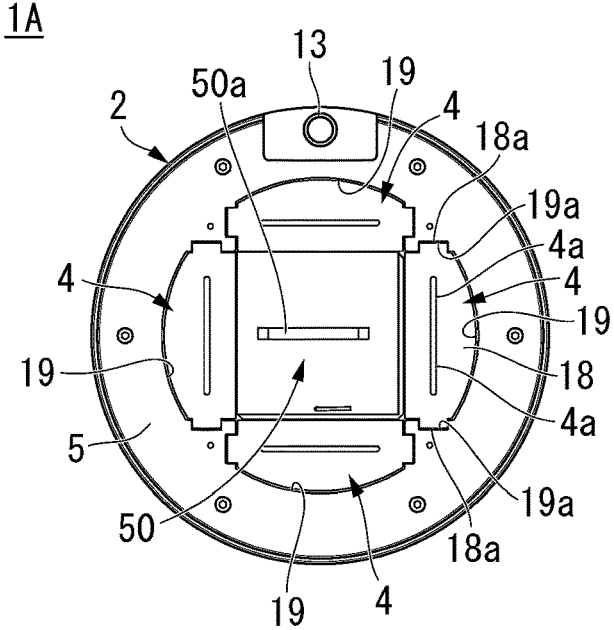
FIG. 3 is a plan view showing a state at which the storage tool in the dry shipper shown in FIG. 1 is housed.
Figure 4:
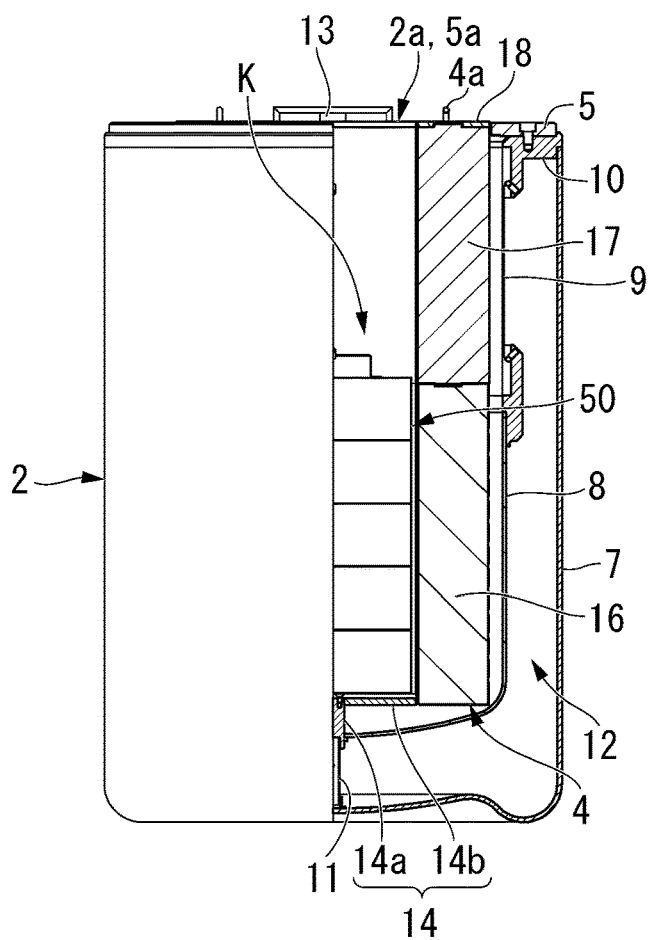
FIG. 4 is a half cross-sectional view showing a state at which the storage tool in the dry shipper shown in FIG. 1 is housed.
Figure 5:
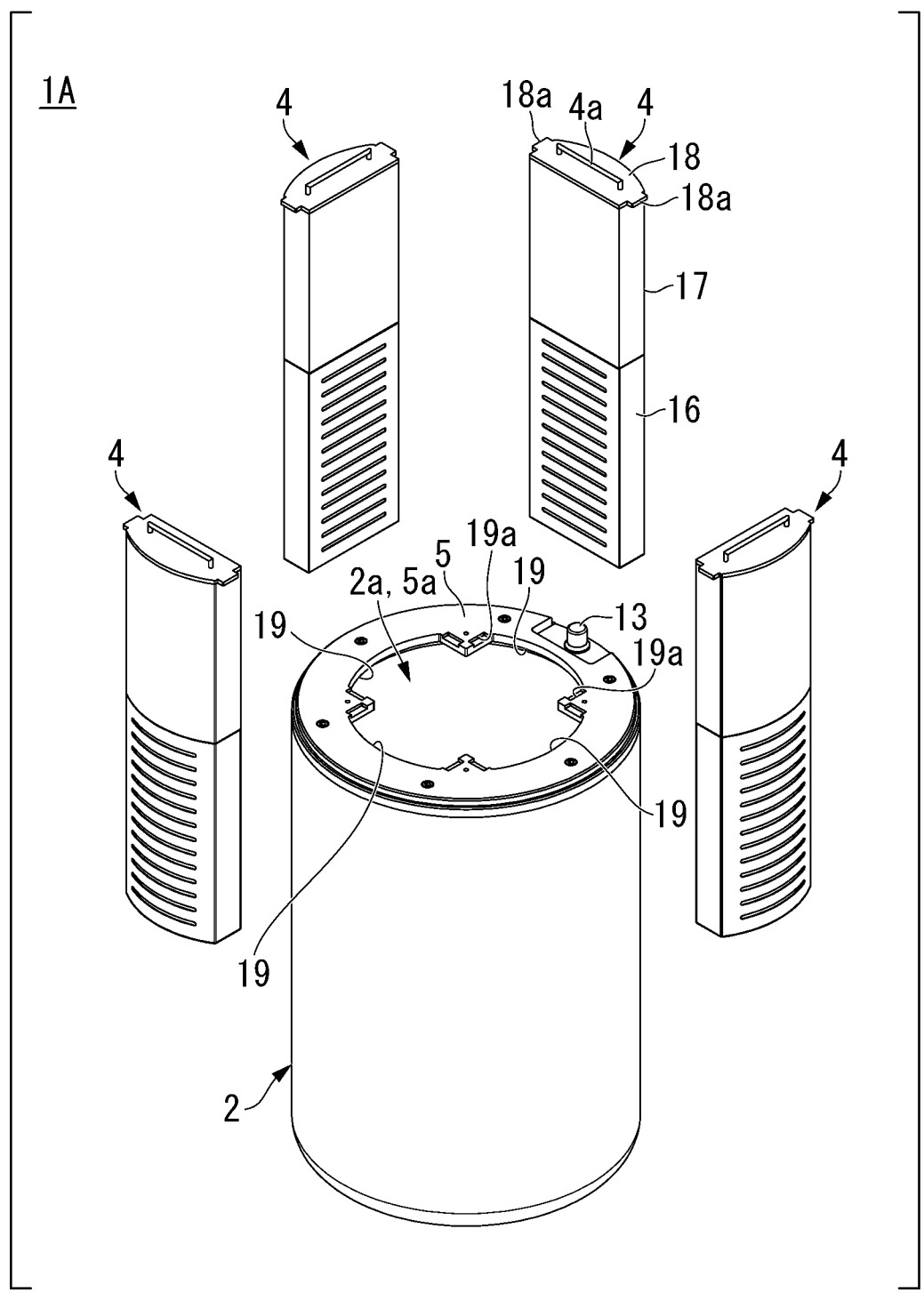
FIG. 5 is an exploded perspective view showing a thermal container and a plurality of cooling units constituting the dry shipper shown in FIG. 1.
Figure 6:
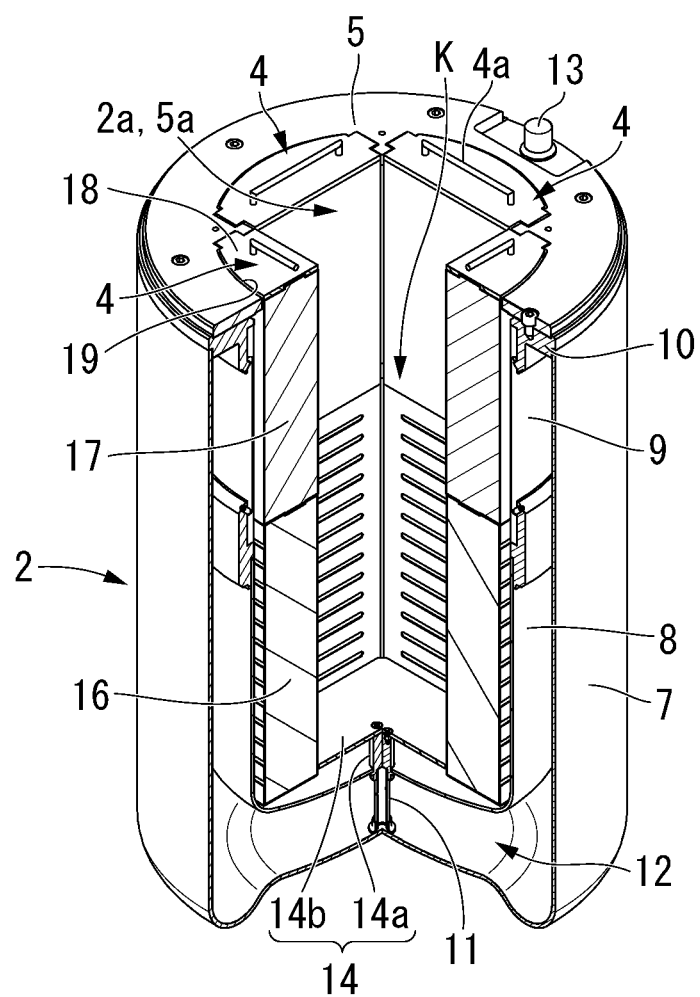
FIG. 6 is a partial cross-sectional perspective view showing a state at which a plurality of cooling units are held in a thermal insulation container.
Figure 7:
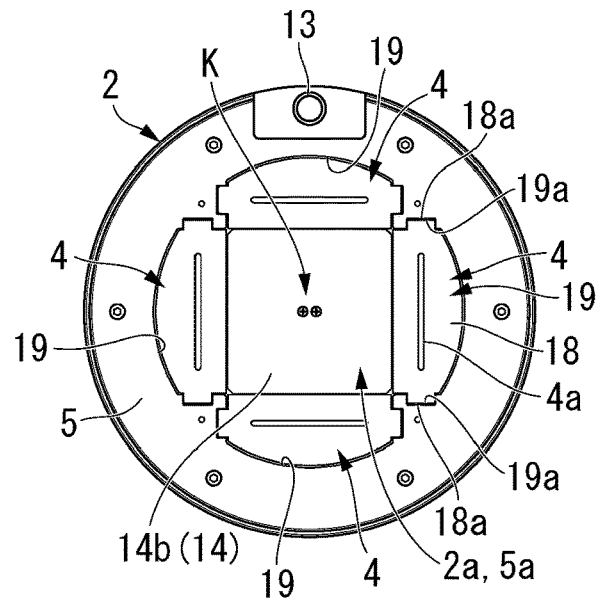
FIG. 7 is a plan view showing a state at which a plurality of cooling units are held in a thermal insulation container.
Figure 8:
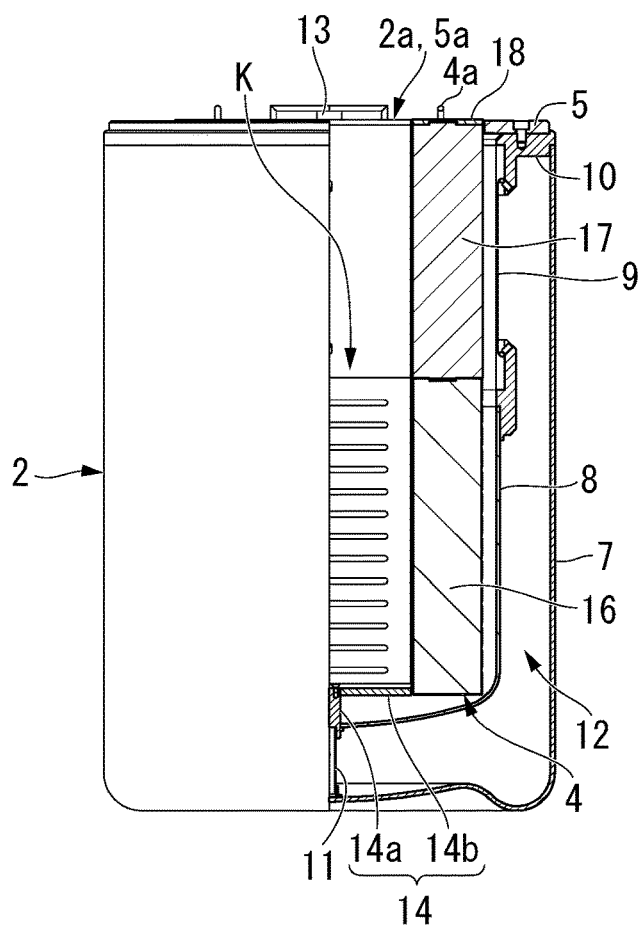
Figure 9:
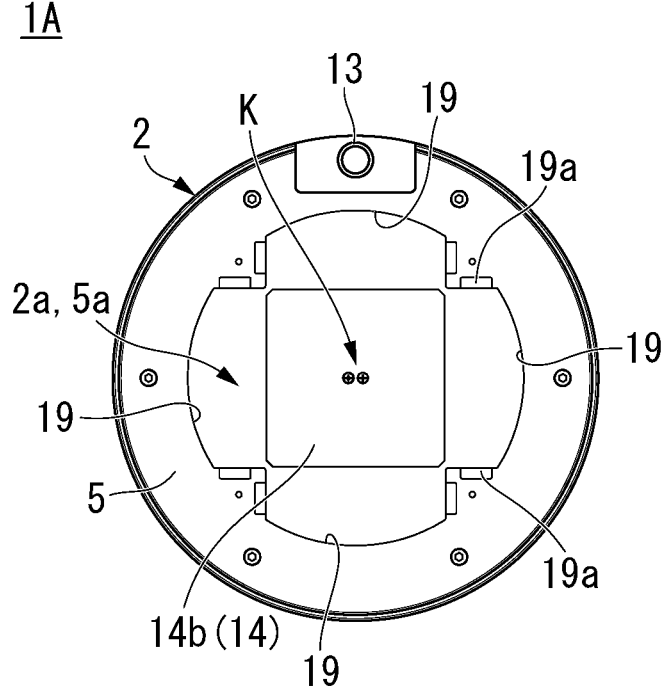
FIG. 9 is a plan view showing a thermal insulation container.
Figure 10:
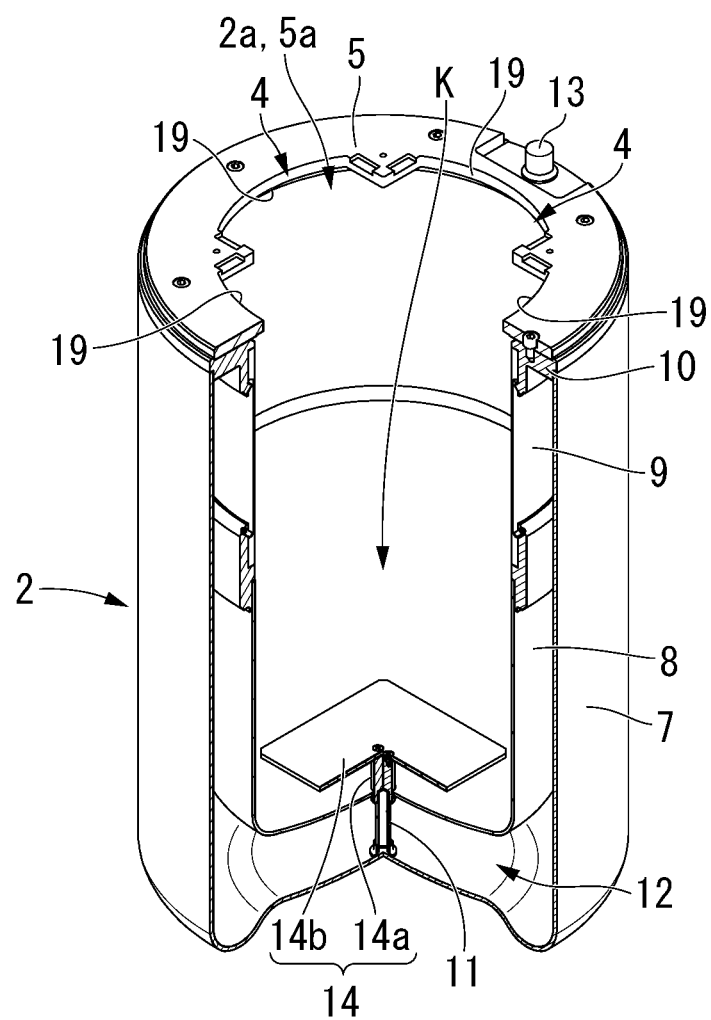
FIG. 10 is a partial cross-sectional perspective view showing a thermal insulation container.
Figure 11:
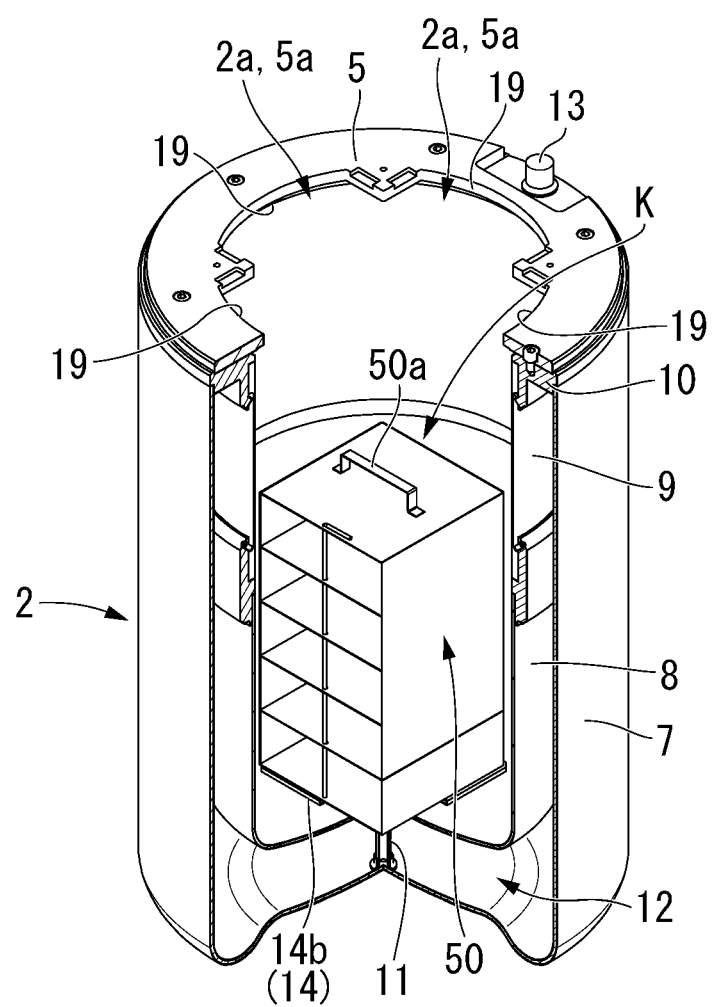
FIG. 11 is a partial cross-sectional perspective view showing a state at which a storage tool is housed in a thermal insulation container with a plurality of cooling units removed.
Figure 12:
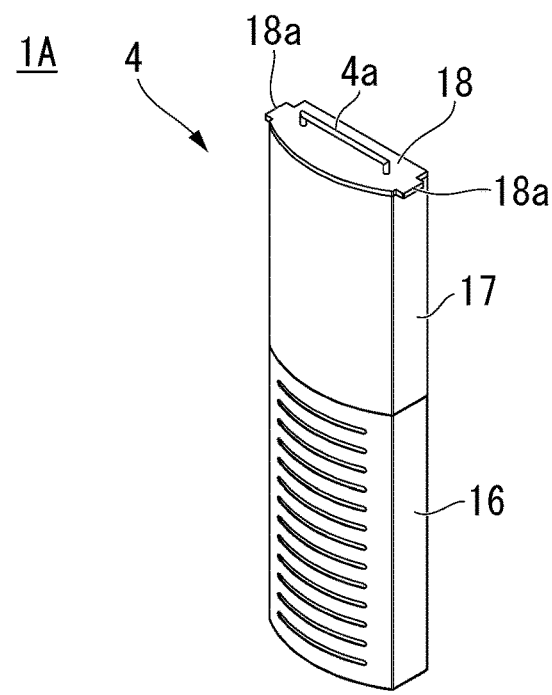
FIG. 12 is a perspective view showing a cooling unit.
Figure 13:
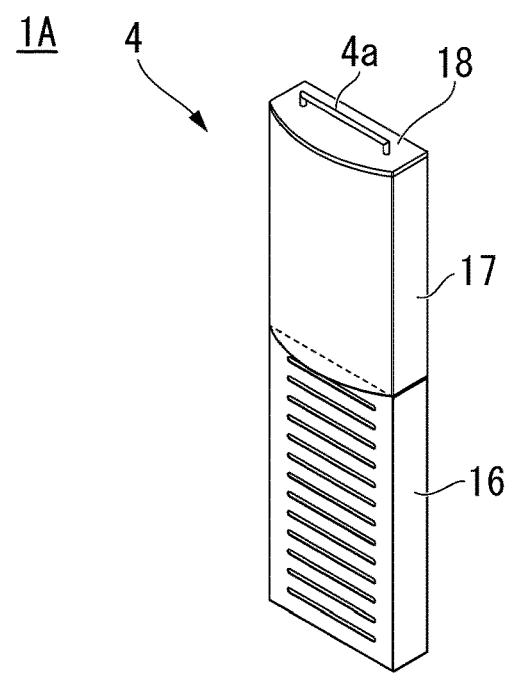
FIG. 13 is a perspective view showing a modified cooling unit.

First, as the first embodiment of the present invention, a dry shipper 1A shown in FIGS. 1 to 13 will be described.
FIG. 1 is an exploded perspective view showing the configurations of a dry shipper 1A and a storage tool 50. FIG. 2 is a partial cross-sectional perspective view showing a state in which the storage tool 50 is housed in the dry shipper 1A. FIG. 3 is a plan view showing a state at which the storage tool 50 is housed in the dry shipper 1A. FIG. 4 is a half cross-sectional view showing a state in which the storage tool 50 is housed in the dry shipper 1A. FIG. 5 is an exploded perspective view showing a thermal insulation container 2 and a plurality of cooling units 4 constituting the dry shipper 1A. FIG. 6 is a partial cross-sectional perspective view showing a state in which the plurality of cooling units 4 are held in the thermal insulation container 2. FIG. 7 is a plan view showing a state in which the plurality of cooling units 4 are held in the thermal insulation container 2. FIG. 8 is a half cross-sectional view showing a state in which the plurality of cooling units 4 are held in the thermal insulation container 2. FIG. 9 is a plan view showing the configuration of the thermal insulation container 2. FIG. 10 is a partial cross-sectional perspective view showing the configuration of the thermal insulation container 2. FIG. 11 is a partial cross-sectional perspective view showing a state in which the storage tool 50 is housed in the thermal insulation container 2 with the plurality of cooling units 4 removed. FIG. 12 is a perspective view showing the configuration of the cooling unit 4. FIG. 13 is a perspective view showing a modified example of the cooling unit 4.

As shown in FIGS. 1 to 4, the dry shipper 1A of the present embodiment is a container for cryopreservation and transportation used for transporting an object to be frozen (not shown). The dry shipper 1A houses the storage tool 50 that stores a plurality of objects to be frozen inside, and transports the objects to be frozen while keeping the inside at an ultra-low temperature (−150° C. or lower) by liquid nitrogen in a vapor phase state.

As shown in FIG. 1, the storage tool 50 is a rack for storing a plurality of objects to be frozen in the vertical direction (height direction). The storage tool 50 is made of a sheet metal such as stainless steel or an aluminum alloy, and has a substantially rectangular parallelepiped shape extending in the vertical direction as a whole. Further, a handle 50a is provided at the upper central portion of the storage tool 50.

The storage tool 50 may be any storage tool as long as it can store objects to be frozen which are to be transported, and is not limited to a rack. Any storage tool such as a drawer or a canister can be used. Further, the configuration of the storage tool 50 is not particularly limited as long as it can be accommodated inside the dry shipper 1A of the present embodiment.

As shown in FIG. 1, the dry shipper 1A of the present embodiment includes the thermal insulation container 2 having an upper opening 2a, a thermal insulation lid 3 for closing the upper opening 2a of the thermal insulation container 2, the plurality of (four in the present embodiment) cooling units 4 which are held in the container 2 in a state of absorbing liquid nitrogen, a guide member 5 which is provided at the upper portion of the thermal insulation container 2, and a pressing member 6 which is detachably provided at the upper portion of the guide member 5.

As shown in FIGS. 9 and 10, the thermal insulation container 2 is a double container having a vacuum insulation structure. Specifically, the container body 2 includes an outer container 7 and an inner container 8 which are bottomed cylindrical shaped, and made of a metal such as an aluminum alloy or stainless steel, a thermal insulation cylinder 9 which is cylindrical shaped, and made of a thermal insulation material such as an epoxy resin, an upper wall plate 10 which is circular ring-shaped, and made of a metal such as an aluminum alloy or stainless steel, and a lower support 11 which is rod-shaped, and made of a thermal insulation material such as an epoxy resin.

In the thermal insulation container 2, the inner container 8 is concentrically housed inside the outer container 7, and a space between the center of the inner bottom surface of the outer container 7 and the center of the outer bottom surface of the inner container 8 is supported by a lower support 11. Further, in a state at which the open end portion of the outer container 7 and the outer peripheral end portion of the upper wall plate 10 are overlapped with each other, the overlapped portions are joined over the entire circumference. The thermal insulation cylinder 9 is attached between the open end of the inner container 8 and the inner peripheral end of the upper wall plate 10 so as to be flush with the inner peripheral surface of the inner container 8.

As a result, the upper end portion of the thermal insulation cylinder 9 is opened in a circular shape in plan view as the upper opening portion 2a of the thermal insulation container 2. Further, the inside of the thermal insulation container 2 is formed in a cylindrical shape toward the bottom of the inner container 8 while maintaining the same diameter as that of the upper opening 2a.

Further, a vacuum thermal insulation layer 12 is provided by the outer container 7, the upper wall plate 10, the inner container 8, and the thermal insulation cylinder 9. The vacuum thermal insulation layer 12 is formed in a high vacuum by degassing from the degassing port (not shown) provided at the upper wall plate 9 and then closing the degassing port with a plug 13.

A support portion 14 for supporting the storage tool 50 is provided inside the thermal insulation container 2. The support portion 14 includes a leg portion 14a that stands upward from the central portion of the bottom surface of the inner container 8, and a support plate 14b attached to the tip of the leg portion 14a. Further, the support plate 14b is formed in a rectangular shape (square shape in the present embodiment) in plan view in accordance with the shape of the storage tool 50. As shown in FIG. 11, the storage tool 50 can be placed on the support plate 14b.

As shown in FIG. 1, the thermal insulation lid 3 is made of a metal such as an aluminum alloy or stainless steel, and includes a top wall portion 3a which is circular shaped in plan view and a peripheral wall 3b which protrudes downward from the periphery of the top wall portion 3a. Further, a thermal insulation convex portion 15 is provided so as to protrude from the central portion of the lower surface of the thermal insulation lid 3. The thermal insulation convex portion 15 is made of a thermal insulation material using a foamed resin such as polystyrene, polyethylene, or polyurethane, and has a length (height) corresponding to that of the thermal insulation cylinder 9, and a substantially rectangular parallelepiped shape extending in the vertical direction as a whole.

As shown in FIGS. 1 to 4 and 6 to 8, a housing space K for accommodating the storage tool 50 is provided inside the thermal insulation container 2. A plurality of cooling units 4 are held in the thermal insulation container 2 in a state of surrounding the housing space K, and are detachably provided into the thermal insulation container 2.

In the dry shipper 1A of the present embodiment, four cooling units 4 are detachably provided at positions surrounding four sides of the housing space K, which is partitioned in a substantially rectangular parallelepiped shape in accordance with the shape of the storage tool 50. Further, in the dry shipper 1A of the present embodiment, when the thermal insulation lid 3 closes the upper opening 2a of the thermal insulation container 2, the thermal insulation convex portion 15 is inserted into the storage space K from above.

As shown in FIG. 12, each cooling unit 4 includes a cooling portion 16 which is provided with an absorbent material that absorbs liquid nitrogen, a thermal insulation portion 17 which is located on the cooling portion 16, and provided with a thermal insulation material, and a positioning portion 18 which is located on the thermal insulation portion 17.

The cooling portion 16 is a case for storing the absorbent material. For example, the cooling portion 16 is made of metal such as an aluminum alloy, stainless steel, or copper, but other materials may be used. Further, on the side surface of the case, slits or holes through which liquid nitrogen passes are provided. As the absorbent material, for example, a resin, fiber, cloth or the like capable of absorbing liquid nitrogen can be used. The cooling portion 16 has a length (height) corresponding to that of the inner container 8, and has a substantially rectangular parallelepiped shape extending in the vertical direction as a whole.

The thermal insulation portion 17 is made of a thermal insulation material using a foamed resin such as polystyrene, polyethylene, or polyurethane, and has a length (height) corresponding to that of the thermal insulation cylinder 9, and a substantially rectangular parallelepiped shape extending in the vertical direction as a whole.

The positioning portion 18 is made of a metal such as an aluminum alloy or stainless steel, has a thickness corresponding to that of the guide member 5, and is formed in a substantially rectangular flat plate shape. Further, the positioning portion 18 is provided with a pair of positioning convex portions 18a protruding from both sides in the width direction.

The cooling unit 4 has a shape in which the outer surface is curved as a whole in accordance with the shape of the thermal insulation container 2, and the inner surface is flat as a whole in accordance with the shape of the housing space K. Further, a handle 4a is provided at the upper portion of the positioning portion 18.

The cooling unit 4 may have a shape in which only the outer surface of the cooling portion 16 is flat, as shown in FIG. 13, for example. This makes it possible to simplify the shape of the case of the cooling portion 16.

As shown in FIGS. 1 to 11, the guide member 5 is made of a metal such as an aluminum alloy or stainless steel, and has a substantially circular flat plate shape as a whole in accordance with the shape of the upper portion of the thermal insulation container 2. The guide member 5 is attached to the upper wall plate 10 by screwing in a state of being overlapped with the upper wall plate 10. The guide member 5 may be integrally formed with the upper wall plate 10. Further, the thermal insulation material explained above or the like may be used for the guide member 5.

An opening 5a is provided at the center of the guide member 5. The opening 5a opens in a substantially circular shape in plan view in accordance with the shape of the upper opening 2a of the thermal insulation container 2.

The guide member 5 has a plurality of (four in this embodiment) guide portions 19 at positions corresponding to each of the plurality of cooling units 4. Each guide portion 19 is cut out in accordance with the shape of the positioning portion 18 of each cooling unit 4. Further, the guide portion 19 is provided with a pair of positioning recesses 19a to which the pair of positioning protrusions 18a are engaged.

In the dry shipper 1A of the present embodiment, each cooling unit 4 is inserted into the inside of the thermal insulation container 2 along each guide portion 19. Further, the cooling unit 4 is guided in the vertical direction of the thermal insulation container 2 along the guide portion 19. By locating the positioning portion 18 inside the guide portion 19, the cooling unit 4 is positioned with respect to the guide member 5.

This makes it possible to hold the cooling unit 4 in the thermal insulation container 2. Further, the housing space K explained above is partitioned inside the plurality of cooling units 4 held in the thermal insulation container 2.

Further, in the dry shipper 1A of the present embodiment, the inner surface of the cooling units 4 which are held in the thermal insulation container 2 is brought into contact with the support plate 14b (support portion 14). Thereby, the movement of the cooling units 4 in the radial direction of the thermal insulation container 2 is restricted. This makes it possible to hold the cooling units 4 in the thermal insulation container 2 in a stable state during transportation of the dry shipper 1A.

The shapes of the guide portion 19 and the positioning portion 18 are not particularly limited to the shapes above, and can be changed as appropriate. Further, in the present embodiment, a positioning convex portion 18a is provided at the positioning portion 18 and a positioning concave portion 19a is provided at the guide portion 19. However, a positioning recess may be provided at the positioning portion 18, and a positioning protrusion may be provided at the guide portion 19. Further, each of the positioning portion 18 and the guide portion 19 may have a positioning convex portion and a positioning concave portion which are engaged with each other.

The pressing member 6 is made of a metal such as an aluminum alloy or stainless steel, and has a substantially circular flat plate shape as a whole in accordance with the shape of the opening 5a of the guide member 5. Further, an opening 6a is provided in the central portion of the pressing member 6. The opening 6a opens in a substantially rectangular shape (square shape in the present embodiment) in plan view in accordance with the shape of the housing space K.

Further, the pressing member 6 has an outer peripheral wall portion 6b protruding downward from the outer periphery thereof, and an inner peripheral wall portion 6c protruding downward from the inner periphery thereof. The outer peripheral wall portion 6b and the inner peripheral wall portion 6c are provided so as to project in accordance with the height of the handle 4a of the cooling unit 4.

The pressing member 6 is fixed to the guide member 5 by screwing while covering the upper portion of the plurality of cooling units 4. The fixing means of the pressing member 6 to the guide member 5 is not limited to such screwing, and any fixing means can be used. Further, the thermal insulation material explained above may be used for the pressing member 6.

In the dry shipper 1A of the present embodiment, the pressing member 6 is brought into contact with each cooling unit 4 held in the thermal insulation container 2, thereby restricting the movement of each cooling unit 4 in the vertical direction of the thermal insulation container 2. This makes it possible to hold the cooling unit 4 in the thermal insulation container 2 in a stable state during transportation of the dry shipper 1A.

Since the pressing member 6 is not always necessary, it may be omitted in some cases. In this case, an arbitrary fixing means for fixing the cooling unit 4 to the guide member 5 may be provided.

In the dry shipper 1A of the present embodiment having the above configuration, while the storage tool 50 located in the housing space K is housed in the thermal insulation container 2, each cooling unit 4 can be individually attached or detached through the upper opening 2a of the thermal insulation container 2.

Therefore, in the dry shipper 1A of the present embodiment, when the amount of liquid nitrogen absorbed by any of the cooling units 4 decreases, it is possible to have the cooling unit 4 reabsorb liquid nitrogen or replace it with another cooling unit 4 that has absorbed liquid nitrogen without removing the storage tool 50 from the thermal insulation container 2.

As a result, it is possible to suppress the temperature rise of an object to be frozen and keep an object to be frozen in a stable state at a low temperature. In addition, it is possible to appropriately control the temperature of an object to be frozen while suppressing the influence on the ambient temperature change.

Further, in the dry shipper 1A of the present embodiment, it is possible to easily remove the plurality of cooling units 4 after use. As a result, operations such as cleaning and disinfection of the inside of each cooling unit 4 and thermal insulation container 2 can be performed easily and in a short time, and excellent maintainability can be obtained.

Second Embodiment

Next, as a second embodiment of the present invention, a dry shipper 1B shown in FIGS. 14 to 17 will be described.

Figure 14:
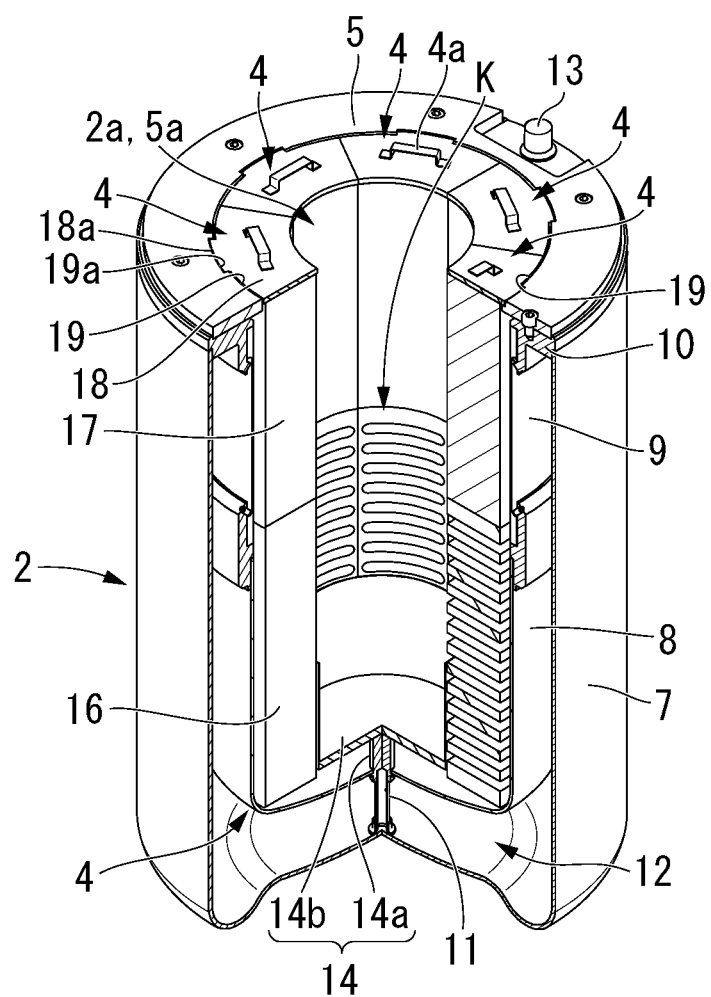
FIG. 14 is a partial cross-sectional perspective view showing a thermal insulation container and a plurality of cooling units constituting a dry shipper according to a second embodiment.
Figure 15:
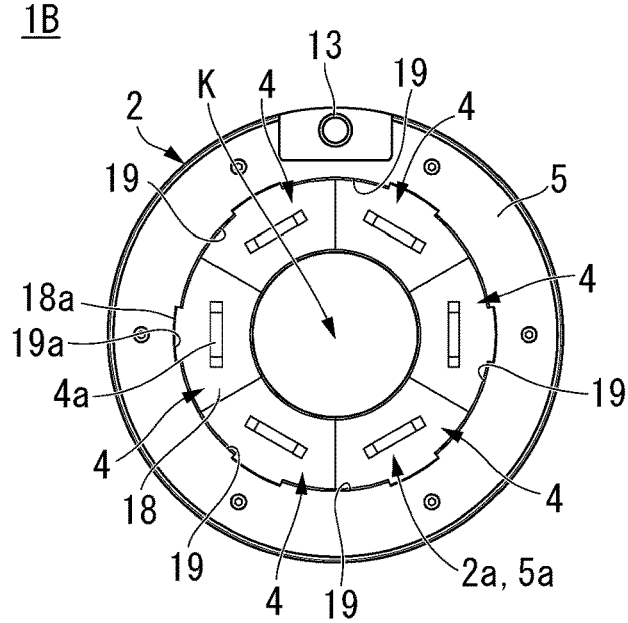
FIG. 15 is a plan view showing a state at which a plurality of cooling units are held in a thermal insulation container.
Figure 16:
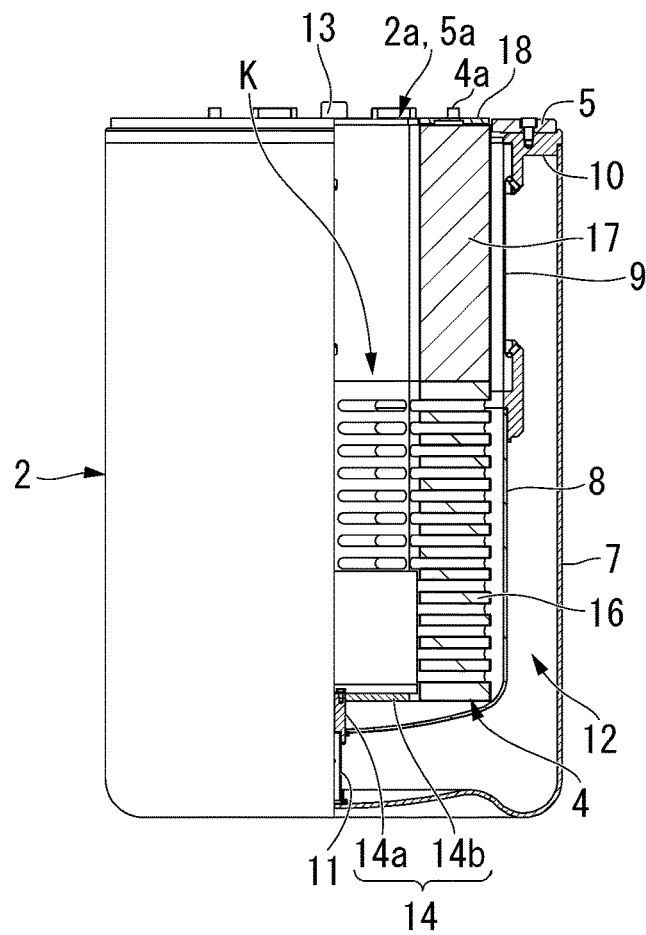
FIG. 16 is a partial cross-sectional view showing a state at which a plurality of cooling units are held in a thermal insulation container.
Figure 17:
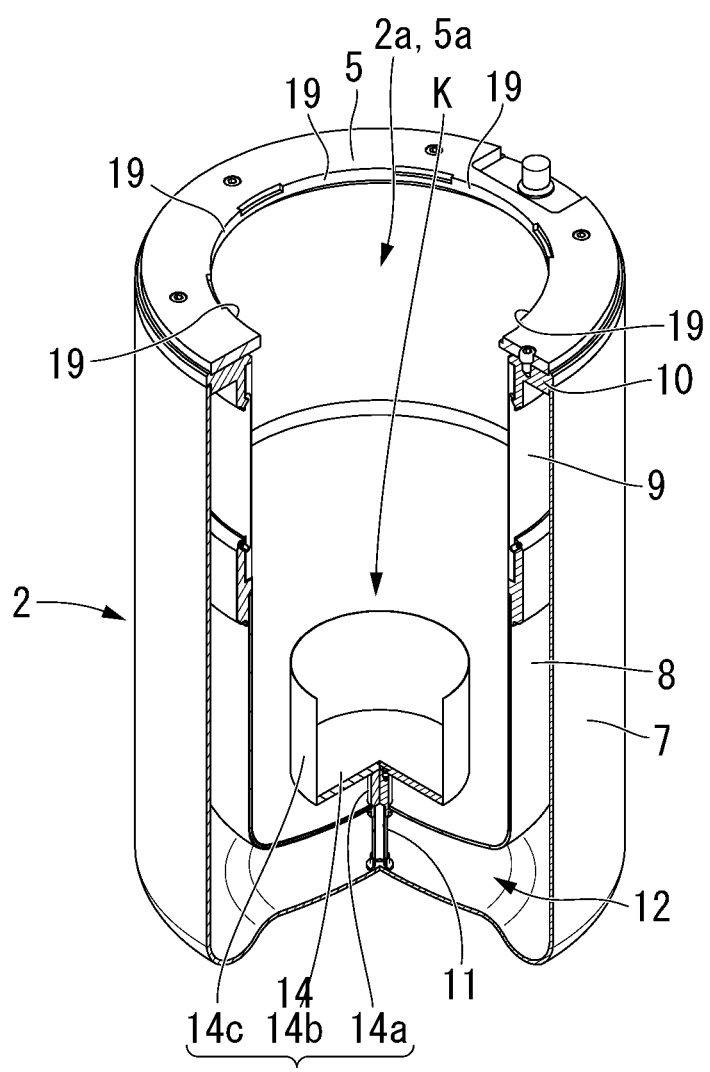
FIG. 17 is a partial cross-sectional perspective view showing a thermal insulation container.

FIG. 14 is a partial cross-sectional perspective view showing a thermal insulation container 2 and a plurality of cooling units 4 constituting the dry shipper 1B. FIG. 15 is a plan view showing a state in which the plurality of cooling units 4 are housed inside the thermal insulation container 2. FIG. 16 is a half cross-sectional view showing a state in which the plurality of cooling units 4 are housed inside the thermal insulation container 2. FIG. 17 is a partial cross-sectional perspective view showing the thermal insulation container 2. Further, in the following description, explanations of the same parts as those of the dry shipper 1A will be omitted, and the same reference numerals will be given in the figures.

As shown in FIGS. 14 to 17, the dry shipper 1B of the present embodiment is provided with a substantially columnar housing space K inside the thermal insulation container 2, and a plurality of (six in the present embodiment) cooling units 4 are detachably held surrounding the housing space K. Other than this structure, the dry shipper 1B has basically the same configuration as that of the dry shipper 1A above.

A support portion 14 of the thermal insulation container 2 has a support plate 14b formed in a circular shape in plan view, and a tubular portion 14c protruding upward from the periphery of the support plate 14b.

Each cooling unit 4 has a shape in which the outer surface is curved as a whole in accordance with the shape of the thermal insulation container 2, and the inner surface is curved as a whole in accordance with the shape of the housing space K. Further, a positioning portion 18 is provided with a positioning convex portion 18a protruding outward from the central portion of the outer peripheral end portion.

A guide member 5 has a plurality of (six in this embodiment) guide portions 19 at positions corresponding to each of the plurality of cooling units 4. The guide portion 19 is provided with a positioning recess 19a with which the positioning protrusion 18a is engaged.

In the dry shipper 1B of the present embodiment, each cooling unit 4 is inserted into the inside of the thermal insulation container 2 along each guide portion 19. Further, the cooling unit 4 is guided in the vertical direction of the thermal insulation container 2 along the guide portion 19, and by locating the positioning portion 18 inside the guide portion 19, the cooling unit 4 is positioned with respect to the guide member 5.

This makes it possible to hold the cooling unit 4 in the thermal insulation container 2. Further, the housing space K above is partitioned inside the plurality of cooling units 4 held in the thermal insulation container 2.

Further, in the dry shipper 1B of the present embodiment, the inner surface of the cooling unit 4 held in the thermal insulation container 2 is in contact with the support plate 14b and the cylindrical portion 14c (support portion 14). This regulates the movement of the cooling unit 4 in the radial direction of the thermal insulation container 2. As a result, it is possible to hold the cooling unit 4 in the thermal insulation container 2 in a stable state during the transportation of the dry shipper 1B.

Although not shown, the storage tool 50 is not particularly limited as long as it can be accommodated inside the dry shipper 1B of the present embodiment (housing space K). Further, the thermal insulation convex portion 15 of the thermal insulation lid 3 has a substantially cylindrical shape extending in the vertical direction as a whole in accordance with the shape of the housing space K. The opening 6a of the pressing member 6 has a circular opening in plan view in accordance with the shape of the housing space K.

In the dry shipper 1B of the present embodiment having the configuration explained above, it is possible to obtain the same effects as those of the dry shipper 1A above. That is, each cooling unit 4 can be individually attached or detached through the upper opening 2a of the thermal insulation container 2 while the storage tool 50 located in the housing space K is housed in the thermal insulation container 2.

Therefore, in the dry shipper 1B of the present embodiment, when the amount of liquid nitrogen absorbed by any of the cooling units 4 decreases, it is possible to have the cooling unit 4 reabsorb liquid nitrogen or replace it with another cooling unit 4 that has absorbed liquid nitrogen without removing the storage tool 50 from the thermal insulation container 2.

As a result, it is possible to suppress the temperature rise of an object to be frozen and keep an object to be frozen in a stable state at a low temperature. In addition, it is possible to appropriately control the temperature of an object to be frozen while suppressing the influence of the ambient temperature change.

Further, in the dry shipper 1B of the present embodiment, it is possible to easily remove the plurality of cooling units 4 after use. As a result, operations such as cleaning and disinfection of the inside of each cooling unit 4 and thermal insulation container 2 can be performed easily and in a short time, and excellent maintainability can be obtained.

Third Embodiment

Next, as a third embodiment of the present invention, a dry shipper 1C shown in FIGS. 18 to 22 will be described.

Figure 18:
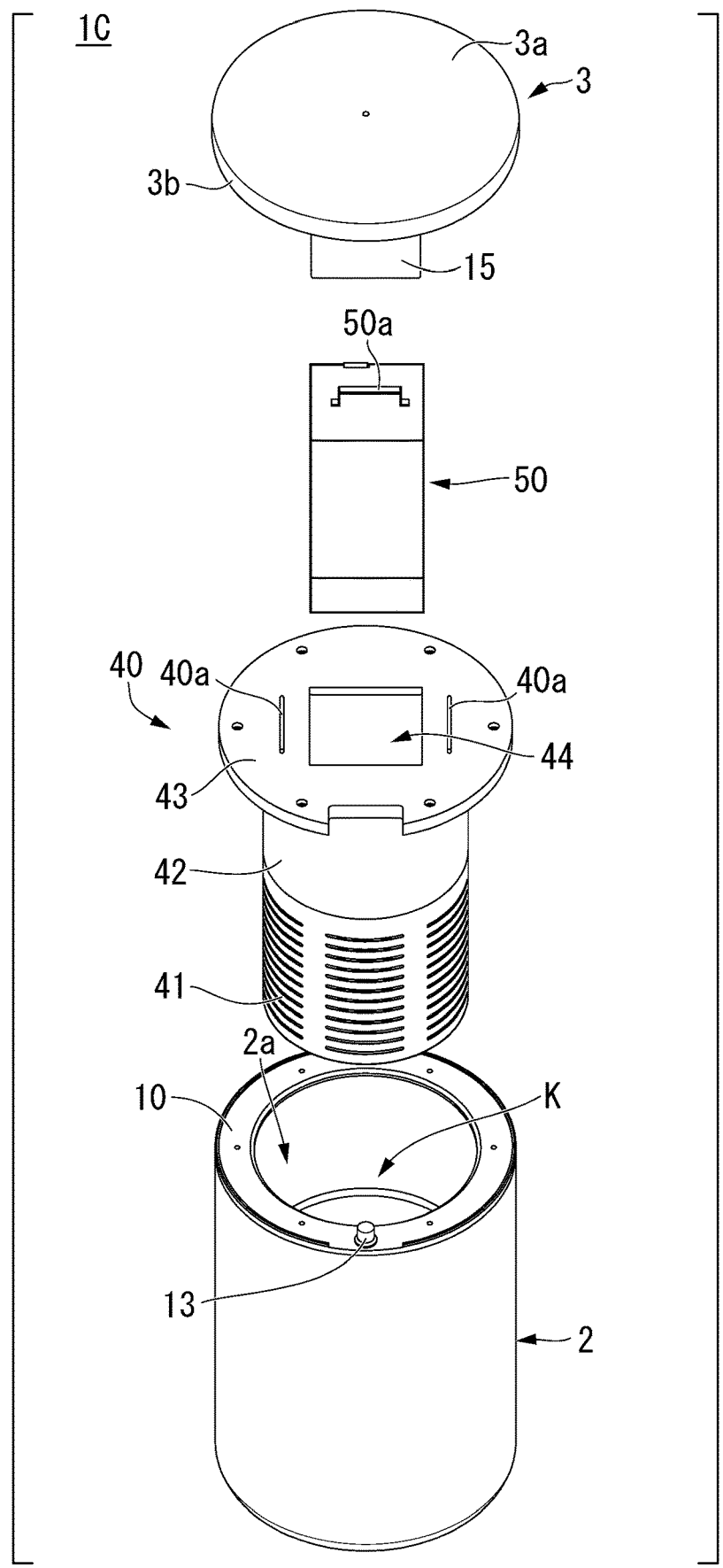
FIG. 18 is an exploded perspective view showing a dry shipper according to a third embodiment of the present invention.
Figure 19:
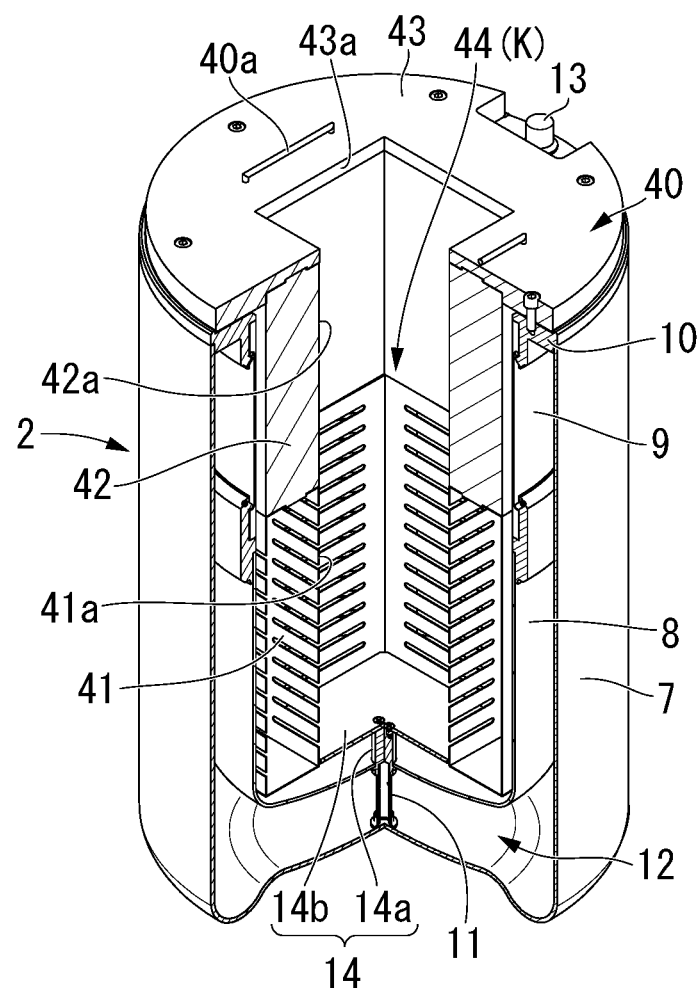
FIG. 19 is a partial cross-sectional perspective view showing a thermal container and a cooling unit constituting the dry shipper shown in FIG. 18.
Figure 20:
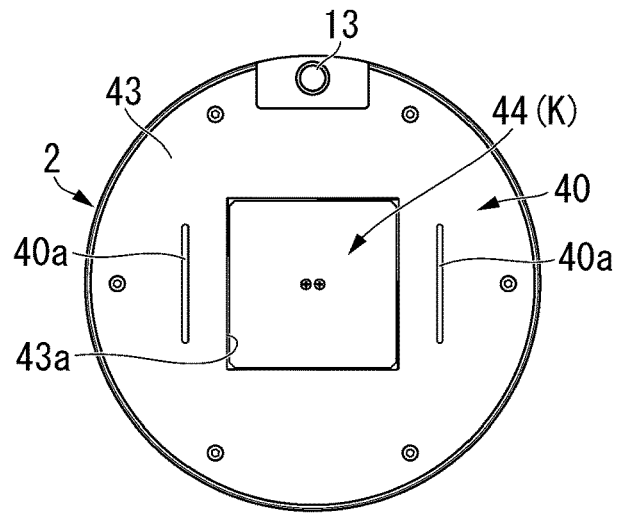
FIG. 20 is a plan view showing a state at which a cooling unit is held in a thermal insulation container.
Figure 21:
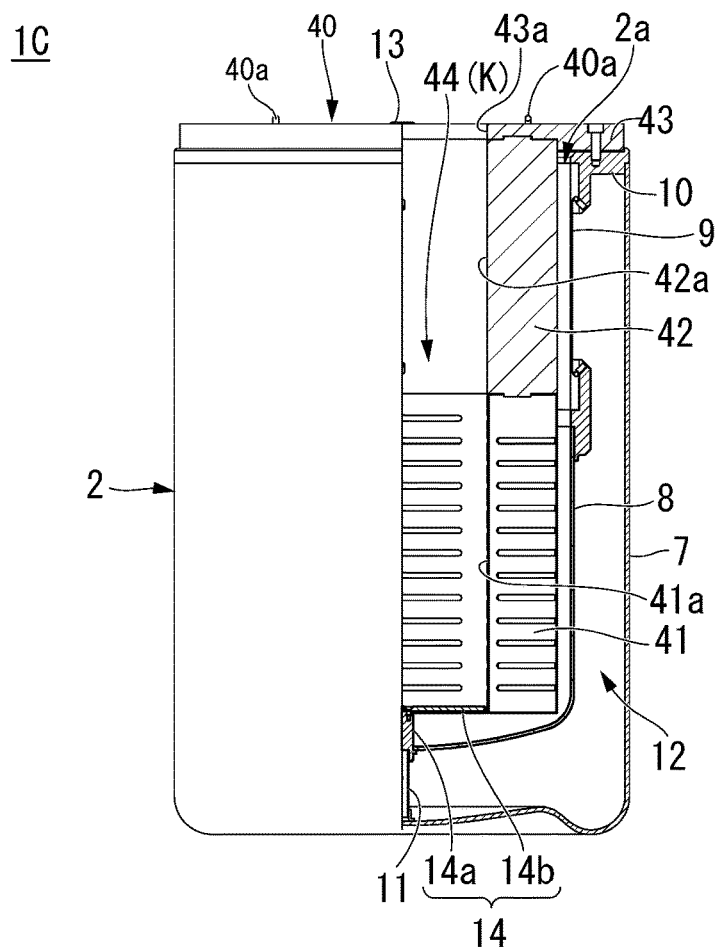
FIG. 21 is a half cross-sectional view showing a state at which a cooling unit is held in a thermal insulation container.
Figure 22:
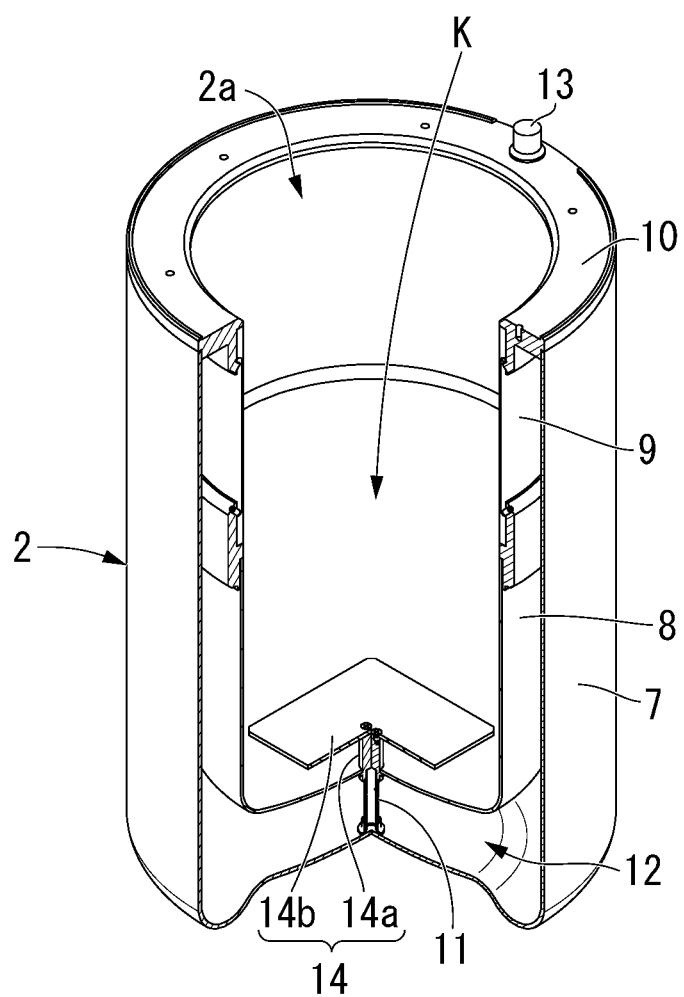
FIG. 22 is a partial cross-sectional perspective view showing a thermal insulation container.

FIG. 18 is an exploded perspective view showing the dry shipper 1C. FIG. 19 is a partial cross-sectional perspective view showing a thermal insulation container 2 and a cooling unit 40 constituting the dry shipper 1C. FIG. 20 is a plan view showing a state in which the cooling unit 40 is held in the thermal insulation container 2. FIG. 21 is a half cross-sectional view showing a state in which the cooling unit 40 is held in the thermal insulation container 2. FIG. 22 is a partial cross-sectional perspective view showing the thermal insulation container 2. Further, in the following description, explanations of the same parts as those of the dry shipper 1A will be omitted, and the same reference numerals will be given in the figures.

As shown in FIGS. 18 to 22, the dry shipper 1C of the present embodiment includes the cooling unit 40 instead of the plurality of cooling units 4. Further, the pressing member 6 is omitted. Other than those, the dry shipper 1C has basically the same configuration as that of the dry shipper 1A above.

The cooling unit 40 includes a cooling portion 41 which is provided with an absorbent material that absorbs liquid nitrogen, a thermal insulation unit 42 which is provided with a thermal insulation material located on the cooling portion 41, a fixing member 43 which is positioned on the thermal insulation container 42, and fixed to the upper portion of the thermal insulation container 2, and a through hole 44 penetrating the central portion of the cooling portion 41, the thermal insulation portion 42, and the fixing member 43 in the vertical direction (height direction).

In the dry shipper 1C of the present embodiment, the housing space K is partitioned in a substantially rectangular parallelepiped shape by the through hole 44. Further, when the thermal insulation lid 3 closes the upper opening 2a of the thermal insulation container 2, the thermal insulation convex portion 15 is inserted into the storage space K (through hole 44) from above.

The cooling portion 41 is a case for storing the absorbent material. For the case, for example, a metal such as an aluminum alloy, stainless steel, or copper can be used, but other materials may be used. Further, on the side surface of the case, slits or holes through which liquid nitrogen passes are provided. As the absorbent material, for example, a resin, fiber, cloth or the like capable of absorbing liquid nitrogen can be used.

The cooling portion 41 has a substantially cylindrical shape extending in the vertical direction as a whole in accordance with the shape of the inside of the inner container 8. Further, in the central portion of the cooling portion 41, a square cylindrical hole portion 41a constituting the through hole 44 is provided so as to penetrate in the vertical direction.

The thermal insulation portion 42 is made of a thermal insulation material using a foamed resin such as polystyrene, polyethylene, or polyurethane, and has a substantially cylindrical shape extending in the vertical direction as a whole in accordance with the shape of the inside of the thermal insulation cylinder 9. Further, in the central portion of the thermal insulation portion 42, a square cylindrical hole portion 42a constituting the through hole 44 is provided so as to penetrate in the vertical direction.

The fixing member 43 is made of a metal such as an aluminum alloy or stainless steel, and has a substantially circular flat plate shape as a whole in accordance with the shape of the upper portion of the thermal insulation container 2. Further, an opening 43a constituting the through hole 44 is provided in the central portion of the fixing member 43. The opening 43a opens in a substantially rectangular shape (square shape in the present embodiment) in plan view in accordance with the shape of the through hole 44 (housing space K). Further, a pair of handles 40a are provided at the upper portion of the fixing member 43.

In the dry shipper 1C of the present embodiment, the cooling unit 40 is inserted into the inside of the thermal insulation container 2 through the upper opening 2a. This makes it possible to hold the cooling unit 40 in the thermal insulation container 2.

Further, in the dry shipper 1C of the present embodiment, the inner surface of the cooling unit 40 which is held in the thermal insulation container 2 is brought into contact with the support plate 14b (support portion 14), so that the movement of the cooling unit 40 in the radial direction of the thermal insulation container 2 is restricted. This makes it possible to hold the cooling unit 40 in the thermal insulation container 2 in a stable state during transportation of the dry shipper 1C.

Further, in the dry shipper 1C of the present embodiment, the fixing member 43 is fixed to the upper wall plate 10 by screwing in a state of being overlapped with the upper wall plate 10. As a result, it is possible to restrict the movement of the cooling unit 40 in the vertical direction of the thermal insulation container 2 and to hold the cooling unit 40 in the thermal insulation container 2 in a stable state during the transportation of the dry shipper 1C.

The fixing means to the upper wall plate 10 of the fixing member 43 is not limited to such screwing, and any fixing means can be used.

In the dry shipper 1C of the present embodiment having the configuration above, it is possible to obtain the same effects as those of the dry shipper 1A above. That is, it is possible to attach or detach the cooling unit 40 through the upper opening 2a of the thermal insulation container 2 while the storage tool 50 located in the housing space K is housed in the thermal insulation container 2.

Therefore, in the dry shipper 1C of the present embodiment, when the amount of liquid nitrogen absorbed by the cooling unit 40 decreases, it is possible to have the cooling unit 40 reabsorb liquid nitrogen or replace it with another cooling unit 40 that has absorbed liquid nitrogen without removing the storage tool 50 from the thermal insulation container 2.

As a result, it is possible to suppress the temperature rise of an object to be frozen and keep an object to be frozen in a stable state at a low temperature. In addition, it is possible to appropriately control the temperature of an object to be frozen while suppressing the influence on the ambient temperature change.

Further, in the dry shipper 1C of the present embodiment, it is possible to easily remove the cooling unit 40 after use. As a result, operations such as cleaning and disinfection of the inside of the cooling unit 40 and thermal insulation container 2 can be performed easily and in a short time, and excellent maintainability can be obtained.

The present invention is not necessarily limited to the embodiments above, and various modifications can be made without departing from the spirit of the present invention.

For example, the cooling unit 4, 40 has a configuration in which the thermal insulation portions 17 and 42 are integrally provided, but the present invention is not limited to such a configuration. The thermal insulation portion 17, 42 may be provided separately from the cooling unit 40.

Further, the cooling unit 40 has a configuration in which the thermal insulation portion 42 and the fixing member 43 are integrally provided, but the present invention is not limited to such a configuration. The fixing member 43 may be provided separately from the cooling unit 40.

EXPLANATION OF REFERENCE NUMERALS 1A, 1B, 1C dry shipper (container for cryopreservation and transportation)
2 thermal insulation container
2a upper opening
3 thermal insulation lid 4 cooling unit
5 guide member
6 pressing member
7 outer container
8 inner container
9 thermal insulation cylinder
10 upper wall plate
11 lower support
12 vacuum insulation layer
13 plug
14 support portion
15 insulation convex portion
16 cooling portion
17 thermal insulation portion
18 positioning portion
19 guide portion
40 cooling unit
41 cooling portion
42 insulation portion
43 fixing member
44 through hole

The invention claimed is:

1. A container for cryopreservation and transportation used to transport an object to be frozen comprising:
a thermal insulation container having an upper opening;
a thermal insulation lid which closes the upper opening of the thermal insulation container; and
a cooling unit which is held in the thermal insulation container while absorbing liquid nitrogen,
wherein a housing space for accommodating a storage tool for storing the object to be frozen is provided inside the thermal insulation container, and
the cooling unit is detachable through the upper opening of the thermal insulation container while the storage tool located in the housing space is housed in the thermal insulation container.

2. The container for cryopreservation and transportation according to claim 1,
wherein the cooling unit is provided with a through hole for partitioning the housing space in the vertical direction.

3. The container for cryopreservation and transportation according to claim 1,
wherein the cooling unit includes a cooling portion which is provided with an absorbent material that absorbs liquid nitrogen, and a thermal insulation portion which is located on the cooling portion and provided with a thermal insulation material.

4. The container for cryopreservation and transportation according to claim 3,
wherein the cooling unit includes a fixing portion which is located on the thermal insulation portion and fixed to the upper portion of the thermal insulation container.

5. The container for cryopreservation and transportation according to claim 1,
wherein a plurality of the cooling units are provided so as to surround the housing space.

6. The container for cryopreservation and transportation according to claim 1,
wherein a support portion for supporting the storage tool is provided at the inner bottom portion of the thermal insulation container.

7. The container for cryopreservation and transportation according to claim 6,
wherein the support portion is in contact with the cooling unit which is held in the thermal insulation container to restrict the movement of the cooling unit in the radial direction of the thermal insulation container.

8. The container for cryopreservation and transportation according to claim 1,
wherein the cooling unit includes a cooling portion which is provided with an absorbent material that absorbs liquid nitrogen, a thermal insulation portion which is provided with a thermal insulation material and located on the cooling portion, and a positioning portion which is located on the thermal insulation portion,
a guide member is provided at the upper portion of the thermal insulation container,
the guide member includes a guide portion having a shape corresponding to the positioning portion, and
the cooling unit is guided in the vertical direction of the thermal insulation container along the guide member, the positioning portion is located inside the guide portion, and the cooling unit is positioned with respect to the guide member.

9. The container for cryopreservation and transportation according to claim 8,
wherein a pressing member is detachably provided at the upper portion of the guide member, and
the pressing member is into contact with the cold insulation unit which is held in the thermal insulation container to restrict the movement of the cold insulation unit in the vertical direction of the thermal insulation container.

10. The container for cryopreservation and transportation according to claim 1,
wherein the thermal insulation lid is provided with a thermal insulation convex portion to be inserted into the housing space.

11. The container for cryopreservation and transportation according to claim 1,
wherein the thermal insulation container has a vacuum insulated structure.

* * * * *